(12) United States Patent
Pan et al.

(10) Patent No.: US 9,260,449 B2
(45) Date of Patent: Feb. 16, 2016

(54) METHOD FOR PREPARING D-BIOTIN

(71) Applicant: Zhejiang Medicine Co., Ltd., Xinchang Pharmaceutical Factory, Shaoxing, Zhejiang (CN)

(72) Inventors: Yajin Pan, Zhejiang (CN); Shiqing Pi, Zhejiang (CN); Wenzhen Ding, Zhejiang (CN); Lixin Gu, Zhejiang (CN); Angfeng Wei, Zhejiang (CN); Yimin He, Zhejiang (CN)

(73) Assignee: ZHEJIANG MEDICINE CO., LTD., XINCHANG PHARMACEUTICAL FACTORY, Xinchang, Shaoxing, Zhejiang (CN)

( * ) Notice: Subject to any disclaimer, the term of this patent is extended or adjusted under 35 U.S.C. 154(b) by 0 days.

(21) Appl. No.: 14/483,147

(22) Filed: Sep. 10, 2014

(65) Prior Publication Data

US 2015/0011777 A1    Jan. 8, 2015

Related U.S. Application Data

(63) Continuation-in-part of application No. 13/321,606, filed as application No. PCT/CN2010/072977 on May 20, 2010, now abandoned.

(30) Foreign Application Priority Data

May 21, 2009  (CN) .......................... 2009 1 0098678
Sep. 9, 2014   (CN) .......................... 2014 1 0456133

(51) Int. Cl.
   *C07D 495/04*    (2006.01)

(52) U.S. Cl.
   CPC .................................... *C07D 495/04* (2013.01)

(58) Field of Classification Search
   CPC ...................................................... C07D 495/04
   See application file for complete search history.

(56) References Cited

PUBLICATIONS

Clercq (Chem. Rev. 1997, 97, 1755-1792).*
Chen et al. (Chemical Research and Application, Jul. 2008, vol. 20, No. 7, p. 913-915; English translation provided).*
Padgett et al. (J. Org. Chem., 1979, v. 44, p. 3492-3496).*

* cited by examiner

*Primary Examiner* — Robert Havlin
(74) *Attorney, Agent, or Firm* — Global IP Services; Tianhua Gu

(57) ABSTRACT

The invention discloses a D-biotin preparation method. In the prior art, with a synthesis method utilizing malonic acid diester as raw materials, impurities are also produced along with the obtained D-biotin. The D-biotin preparation method is characterized in that with the presence of dimethyl sulfoxide and inorganic base as catalysts, methane tricarboxylic acid trialkyl ester and (3aR, 8aS, 8bS)-1,3-dibenzyl-2-oxo-10H-iminazole [3,4-d] thiophene [1,2-a] sulfuryl halide are subjected to condensation reaction in methylbenzene solvent to obtain intermediate (3 aS,4S,6aR)-1,3-dibenzyl-4-(ω,ω,ω-3-methoxycarbonylbutyl)-4H-1H-thiophene[3,4-d]iminazole-2,4(1H)-ketone, and the D-biotin is obtained after the intermediate is treated by the aftertreatment method. By the D-biotin preparation method, production of the impurities is avoided, quality of the biotin is greatly improved on the existing basis, and side reaction is avoided too.

4 Claims, No Drawings

METHOD FOR PREPARING D-BIOTIN

CROSS REFERENCE TO RELATED PATENT APPLICATION

The present application is a continuation in part application of the U.S. application Ser. No. 13/321606 filed on Nov. 21, 2011, which is incorporated herein by reference and this application claims a priority of CN application 201410456133.X filed on Sep. 9, 2014. The U.S. application Ser. No. 13/321606 is an U.S. national stage of PCT/CN2010/072977 filed on May 20, 2010, which claims the priority of the Chinese patent application No. 200910098678.7 filed on May 21, 2009.

TECHNICAL FIELD

The invention relates to the field of biotin preparation, in particular to a D-biotin preparation method.

BACKGROUND

The D-Biotin, also known as Vitamin H, is mainly applied to the fields of medicine and sanitation, nutrition enhancer, feed additive, cosmetics and drinks, etc. The molecular structural formula of the D-Biotin is shown as follows:

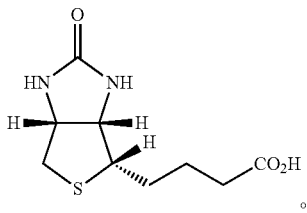

Since the debut of industrially-synthetized D-biotin of a Swiss company Roche in 1949, the synthesis methods have been still undergone many researches abroad. To date, many about total synthesis routes have been reported. Yet, the Sternbach route with thiolactone as a key intermediate still remains the recognition of the most industrial significance.

The Sternbach route includes that thiolactone 2 with optical activity is used as a starting material, the key intermediate (3aR,8aS,8bS)-1,3-dibenzyl-2-oxo-10H-iminazole [3,4-d] thiophene [1,2-a] sulfuryl halide 3 is obtained by several steps of reaction, and with the presence of base, bromide 3 and diethyl malonate are reacted to obtain an intermediate 4, the intermediate 4 is kept treated by hydrobromic acid (including several steps of esterolysis, decarboxylation and debenzylation), and finally the biotin 1 is obtained by cyclization. The Sternbach systhesis route is drawn as follow.

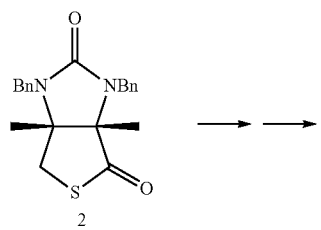

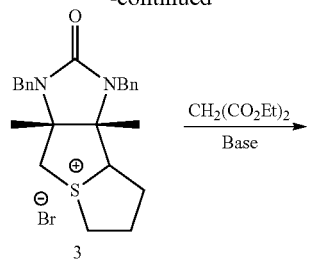

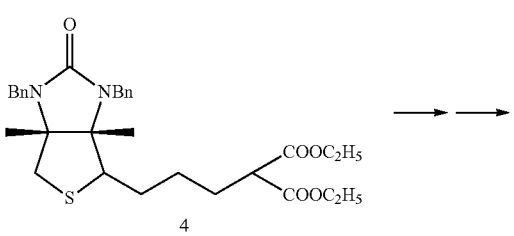

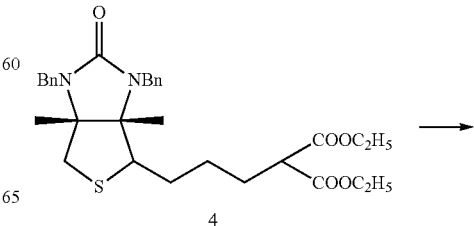

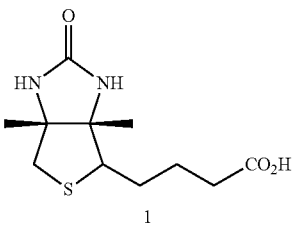

In the condensation process of the bromide 3 and malonic diester, since the malonic diester comprises two reactive hydrogens, when the intermediate 4 is obtained after the malonic diester is reacted with the bromide 3, impurities 5 are also produced in the train of further reaction between the intermediate 4 and the bromide 3 under the action of the base. The impurities 5 are hydrolyzed, decarboxylated, debenzylated and cyclized together with the common intermediate 4, thus, the finally obtained biotin 1 should be doped with impurities 6. Though researchers have successfully attempts to reduce the impurities 6 by increasing proportion of the malonic diester and reduce content of the impurities in the product by a recrystallizing method, yet the impurities are unlikely to be completely removed from the finished biotin. So production of the impurities is a kind of technical defect in this route. Besides, the production mechanism and the chemical formula of the impurities are shown as follow.

-continued

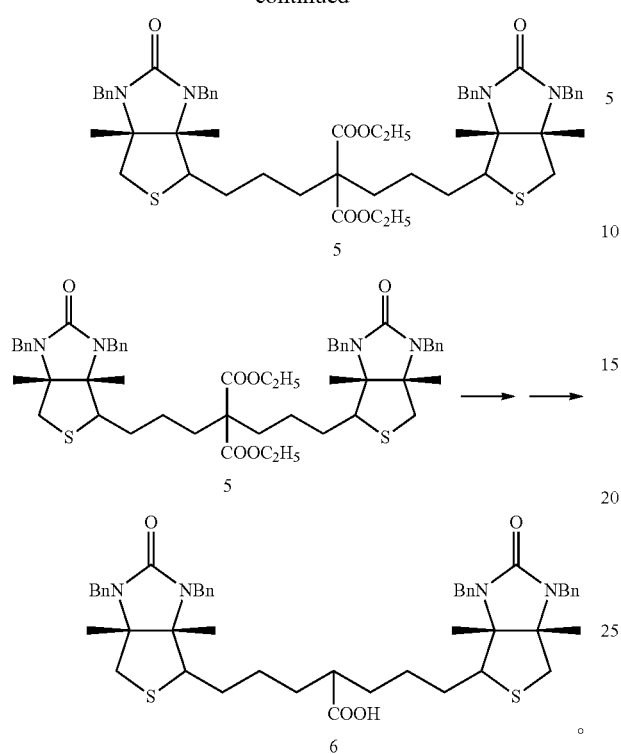

5

6

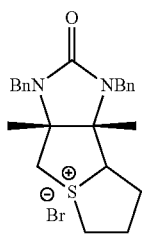

Formula B

The aftertreatment method adopted as the prior art mainly includes heating the intermediate in the hydrobromic acid to hydrolyze tricarboxylic acid ester to be tricarboxylic acid compounds, unstably decarboxylating the tricarboxylic acid compounds with acid in the heating state to be double-benzyl biotin only comprising one carboxyl, heating the double-benzyl biotin in the hydrobromic acid to remove benzyl and generate the biotin, de-cyclizing five-member circles of part of the biotin in the process of debenzylation, and finally completely converting to obtain the D-biotin through the cyclization.

In the D-biotin preparation method, the malonic diester is substituted by the methane tricarboxylic ester. As methyne in the methane tricarboxylic ester only contains one reactive hydrogen, only one product 7 can be produced when the reactive hydrogen and the bromide which is the intermediate are in substitution reaction under the action of the catalysts and the impurities 5 are by no means generated. The finished biotin 1 is of course free of impurities 6. Therefore, quality of the biotin is greatly improved on the existing basis, and since side reactions are avoided, utilization efficiency of the intermediate Bromide is improved as well. The specific reaction formula of the preparation method is attached as follow.

CONTENT

The invention aims to solve the technical problem of overcoming the defects in the existing synthesis routes and provides the D-biotin preparation method. The D-biotin preparation method is the one improved from the chemical mechanism, thereby being capable of preventing production of the impurities.

For this purpose, the technical scheme includes that the D-biotin preparation method is characterized in that with the presence of catalysts including dimethyl sulfoxide and inorganic base, methane tricarboxylic acid trialkyl ester and (3aR, 8aS,8bS)-1,3-dibenzyl-2-oxo-10H-iminazole [3,4-d] thiophene [1,2-a] sulfuryl halide (Formula B) are subjected to condensation reaction in methylbenzene solvent to obtain intermediate (3aS,4S,6aR)-1,3 -dibenzyl-4-(ω,ω,ω-3-methoxycarbonylbutyl)-4H- 1H-thiophene[3 ,4-d]iminazol e-2,4 (1H)-ketone (Formula A) and the D-biotin is obtained after the intermediate is treated by the aftertreatment method, wherein usage of the dimethyl sulfoxide is 5-10% of that of the methylbenzene solvent.

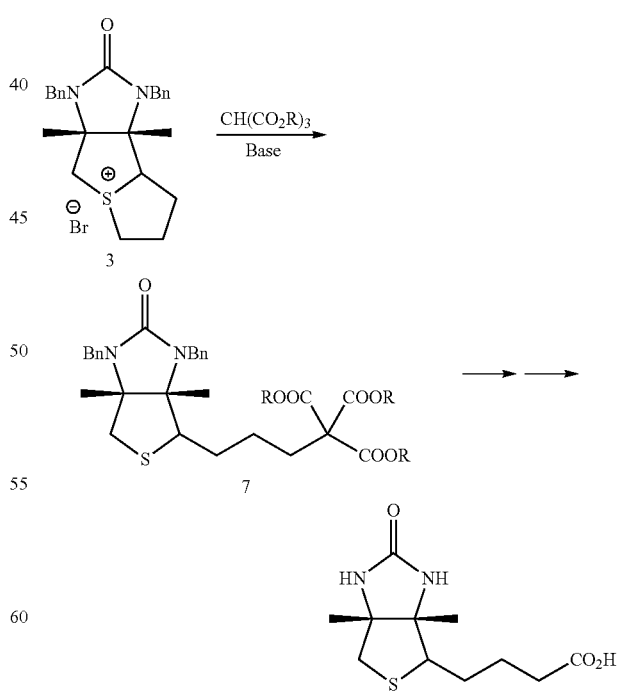

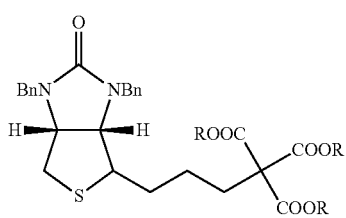

Formula A

The methane tricarboxylic acid trialkyl ester in the D-biotin preparation method substitutes for the malonic diester. Compared with the existing malonic diester route, the D-biotin preparation method is mostly differentiated by two aspects. More specifically, the product is free of the impurities 5 and the impurities 6 related before; reaction conditions for the methane tricarboxylic acid trialkyl ester differs greatly from the malonic diester, for example, during practical operation, the malonic diester and the base in the methylbenzene as solvent generate anions at first, and the generated alkyl anions are further substitutionally reacted with the bromide to obtain the key intermediate 4. However, when the malonic diester is changed into the methane tricarboxylic acid trialkyl ester, no any reactions happen. To his surprise, the inventor found that reactions can smoothly come up and a key intermediate 7 is obtained if a certain amount of the catalyst DMSO (dimethyl sulfoxide) is added, and this is the second aspect different from the malonic diester route.

The DMSO functions in reacting with the inorganic base which can be sodium hydride or potassium hydride to obtain DMSO sodium salt or kali salt and smoothly capturing methyne hydrogen on the methane tricarboxylic acid trialkyl ester to promote condensation reaction; in changing polarity of the solvent to increase dissolvability of sulfonium onium salt in the reaction solvent.

Experiments showed that if usage of the DMSO is 5% lower than that of the methylbenzene, reaction is incapable of being carried through; if the catalyst DMSO is higher than 10%, the reaction can take place, but difficulty in aftertreatment is consequently increased and yield is dramatically reduced. If the incremental usage of the DMSO is higher than 10%, difficulty in the process of recovering the solvent after reaction may arise. High boiling point of the DMSO and the solid product may result in low recovery rate of the DMSO, and even, in the subsequent treatment procedure, the DMSO and the inorganic salt is dissolved in waste water, as a result, economic efficiency is low and waste-water environmental protection treatment is complicated. Therefore, the usage of the catalyst is preferably 5-10% of that of the methylbenzene solvent.

The chemical formula of the methane tricarboxylic acid trialkyl ester is $CH(COOR)_3$, wherein the R is preferably the alkyl group comprising 1-5 carbon atoms. Further, the Rs on three carboxylic acid groups are same or different alkyl groups, and the R is most preferably methyl or ethyl.

The inorganic base is preferably sodium hydride or potassium hydride, for other organic bases such as sodium methoxide, sodium ethoxide, sodium tert-butoxide, potassium methoxide, potassium ethoxide or potassium tert-butoxide are low in reaction yield and have no industrialized significance.

The D-biotin preparation method specifically includes steps of 1) suspending the sodium hydride or potassium hydride in the methylbenzene and dripping the dimethyl sulfoxide as the catalyst at the room temperature to obtain mixture; 2) dripping the methylbenzene solvent of the methane tricarboxylic acid trialkyl into the mixture to react and obtain methane tricarboxylic acid trialkyl sodium or methane tricarboxylic acid trialkyl potassium; 3) adding the solid (3aR,8aS,8bS)-1,3-dibenzyl -2-oxo-10H-iminazole [3,4-d] thiophene [1,2-a] sulfuryl halide (Formula B) into the product obtained in the step 2), heating to 80-110 DEG C to react, sampling and detecting and stopping after complete reaction; 4) performing aftertreatment, to be specifically, rinsing to layer, recycling the methylbenzene, adding hydrobromic acid to hydrolyze and obtain carboxylic acid, decarboxylating and debenzylating simultaneously, and finally cyclizing and purifying to obtain the D-biotin.

Compared with existing methods, the D-biotin preparation method has the advantages that production of the impurities 6 is avoided, quality of the biotin is greatly improved on the existing basis, side reactions are avoided, and utilization efficiency of the bromide 3 as the intermediate is greatly improved as well.

Concrete Embodiments

The following embodiments are used for elaborating the D-biotin preparation method, and given parameters in the embodiments are not assumed as limitations for the D-biotin preparation method.

Embodiments (of Existing Methods) for Comparison

A. Synthesis of (3aS,4S,6aR)-1,3-dibenzyl-4-(ω,ω,ω-3-methoxycarbonyl butyl)-4H-1H-thiophene [3, 4-d]iminazole-2, 4(1H)-ketone (the intermediate 4)

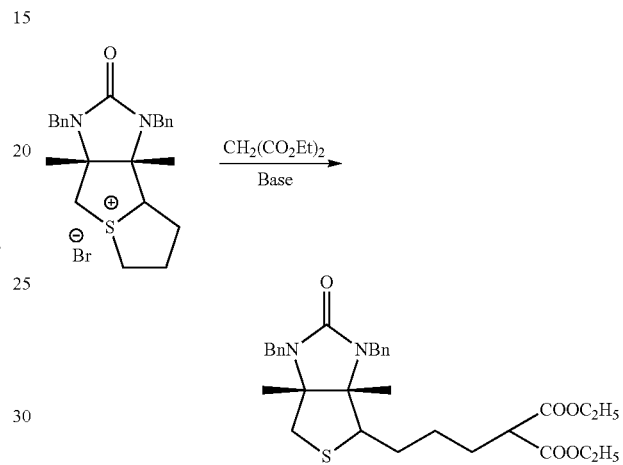

In a dry nitrogen-protection four-neck flask 500 ml with a reflux condenser, a dripping tube, a stirrer and a thermometer, the synthesis steps include adding 300 ml of methylbenzene and 60% of sodium hydride 6.0 g(0.15 mol), controlling the inner temperature below 80 DEG C and dripping malonic acid diethyl ester 48 g(0.3 mol), keeping heat preservation for 2 hours after dripping, cooling to the room temperature, adding bromine sulfonium onium salt 33.3 g (0.075 mol), heating and preserving and controlling the temperature at 80 DEG C to react for 15 hours, cooling to the room temperature, adjusting the pH (potential of hydrogen) to be around 3 by 5% of sulfuric acid, layering to obtain an organic layer, layering to obtain a water layer through reextraction by methylbenzene 100 mL, integrating the water layer into the organic layer, washing the organic layer twice by 5% of sodium bicarbonate water solution 40 mL, drying an oil layer by anhydrous sodium sulfate, filtering, depressurizing and recovering to obtain faint yellow liquid and getting a target product, diester dibenzyl biotin 37 g(94.1% of the theoretical value) in the content 94.5% measured by HPLC (high performance liquid chromatorgraphy) and with 3.5% of the impurities 5 (hereinafter referred as. dicarboxylic ester).

B. Synthesis of the D-Biotin

In a three-neck flask 2000 mL, the synthesis steps of the D-biotin include injecting the above-mentioned diester dibenzyl biotin 37g and 48% of hydrobromic acid 800 g, stirring, refluxing and preserving the temperature at 125-126 DEG C for 8 hours, tracking the reaction until reaction (developer is methylbenzene—glacial acetic acid—methyl alcohol in the ratio 10:10:3(v/v/v)) is completed by the thin layer method, recovering the hydrobromic acid in vacuum, adjusting pH of residues to be 8 to 9 by 10% of sodium hydroxide, and cooling to be below 20 DEG C; weighing Bis(trichloromethyl) carbonate (BTC) 16 g to be dissolved by the methylbenzene 150 mL, slowly dripping the dissolved BTC into the above solution, keeping controlling the pH of the water layer to be 8 to 9 by the base during dripping, stirring for 1 hour after dripping, separating the organic layer, adjusting the pH of the water layer to be faintly acid by 10% of hydrochloric acid, precipitating to obtain crude biotin, recrystallizing the crude biotin by water and drying to obtain pure biotin 13.5 g in the content 96.5% measured by the HPLC and with 1.2% of the impurities 6 (hereinafter referred as dicarboxylic acid).

Embodiment 1

A. Synthesis of (3aS,4S,6aR)-1,3-dibenzyl-4-(ω,ω,ω-3-methoxycarbonyl butyl)-4H-1H-thiophene [3, 4-d]imina-zole-2, 4(1H)-ketone (Formula A) (the intermediate 7)

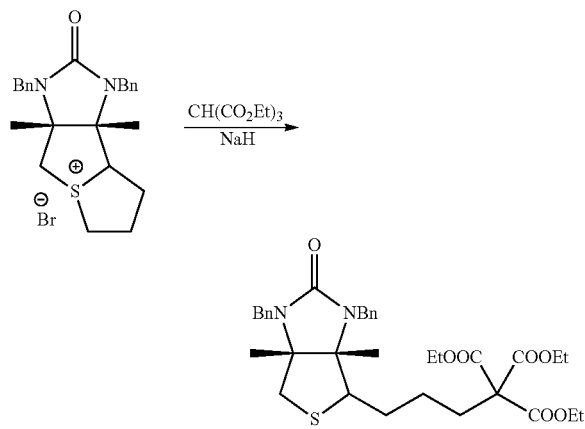

In a dry nitrogen-protection four-neck flask 500 ml with a reflux condenser, a dripping tube, a stirrer and a thermometer, the synthesis steps include adding 300 ml of methylbenzene and 60% of sodium hydride 3.3 g(0.0825 mol), dripping the catalyst 15 mL, controlling the inner temperature below 80 DEG C and dripping methane tricarboxylic acid trialkyl 19.3 g(0.083 mol), keeping heat preservation for 2 hours after dripping, cooling to the room temperature, adding bromine sulfonium onium salt 33.3 g (0.075 mol), heating and preserving and controlling the temperature at 80 DEG C to react for 15 hours, cooling to the room temperature, adjusting the pH to be around 3 by 5% of sulfuric acid, layering to obtain an organic layer, layering to obtain a water layer through reextraction by methylbenzene 100 mL, integrating the water layer into the organic layer, washing the organic layer twice by 5% of sodium bicarbonate water solution 40 mL, drying an oil layer by anhydrous sodium sulfate, filtering, depressurizing and recovering to obtain faint yellow liquid and getting a target product, tri-ester dibenzyl biotin 42.5 g(95.5% of the theoretical value) in the content 97.8% measured by HPLC and without the impurities 5.

B. Synthesis of the D-Biotin

In a three-neck flask 2000 mL, the synthesis steps of the D-biotin include injecting 42.5 g of the above-mentioned tri-ester dibenzyl biotin 7 and 48% of hydrobromic acid 800 g, stirring, refluxing and preserving the temperature at 125-126 DEG C for 8 hours, tracking the reaction until reaction (developer is methylbenzene—glacial acetic acid—methyl alcohol in the ratio 10:10:3(v/v/v)) is completed by the thin layer method, recovering the hydrobromic acid in vacuum, adjusting pH of residues to be 8 to 9 by 10% of sodium hydroxide, and cooling to be below 20 DEG C; weighing Bis(trichloromethyl) carbonate (BTC) 16 g to be dissolved by the methylbenzene 150 mL, slowly dripping the dissolved BTC into the above solution, keeping controlling the pH of the water layer to be 8 to 9 by the base during dripping, stirring for 1 hour after dripping, separating the organic layer, adjusting the pH of the water layer to be faintly acid by 10% of hydrochloric acid, precipitating to obtain crude biotin, filtering, recrystallizing the crude biotin by water and drying to obtain pure biotin 13.8 g in the content 98.8% measured by the HPLC and without the impurities 6 in the product.

Embodiment 2

A. Synthesis of (3aS,4S,6aR)-1,3-dibenzyl-4-(ω,ω,ω-3-methoxycarbonyl butyl)-4H-1H-thiophene [3,4-d]imina-zole-2,4(1H)-ketone (Formula A) (the intermediate 7)

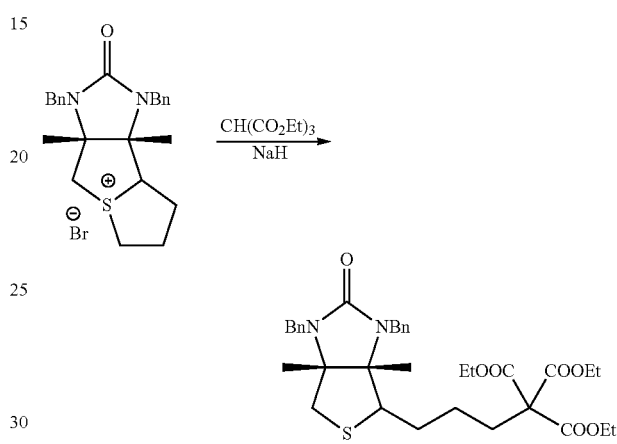

In a dry nitrogen-protection four-neck flask 500 ml with a reflux condenser, a dripping tube, a stirrer and a thermometer, the synthesis steps include adding 300 ml of methylbenzene and 60% of sodium hydride 3.3 g(0.0825 mol), dripping the catalyst 20 mL, controlling the inner temperature below 80 DEG C and dripping methane tricarboxylic acid trialkyl 19.3 g(0.083 mol), keeping heat preservation for 2 hours after dripping, cooling to the room temperature, adding bromine sulfonium onium salt 33.3 g (0.075 mol), heating and preserving and controlling the temperature at 80 DEG C to react for 15 hours, cooling to the room temperature, adjusting the pH to be around 3 by 5% of sulfuric acid, layering to obtain an organic layer, layering to obtain a water layer through reextraction by methylbenzene 100 mL, integrating the water layer into the organic layer, washing the organic layer twice by 5% of sodium bicarbonate water solution 40 mL, drying an oil layer by anhydrous sodium sulfate, filtering, depressurizing and recovering to obtain faint yellow liquid and getting a target product, tri-ester dibenzyl biotin 42.5 g(95.5% of the theoretical value) in the content 98.0% measured by HPLC and without the impurities 5.

B. Synthesis of the D-Biotin

In a three-neck flask 2000 mL, the synthesis steps of the D-biotin include injecting 42.5 g of the above-mentioned tri-ester dibenzyl biotin 7 and 48% of hydrobromic acid 800 g, stirring, refluxing and preserving the temperature at 125-126 DEG C for 8 hours, tracking the reaction until reaction (developer is methylbenzene—glacial acetic acid—methyl alcohol in the ratio 10:10:3(v/v/v)) is completed by the thin layer method, recovering the hydrobromic acid in vacuum, adjusting pH of residues to be 8 to 9 by 10% of sodium hydroxide, and cooling to be below 20 DEG C; weighing Bis(trichloromethyl) carbonate (BTC) 16 g to be dissolved by the methylbenzene 150 mL, slowly dripping the dissolved BTC into the above solution, keeping controlling the pH of the water layer to be 8 to 9 by the base during dripping, stirring for 1 hour after dripping, separating the organic layer, adjusting the pH of the water layer to be faintly acid by 10% of hydrochloric acid, precipitating to obtain crude biotin, filtering, recrystallizing the crude biotin by water and drying to obtain pure biotin 13.9 g in the content 98.7% measured by the HPLC and without the impurities 6 in the product.

Embodiment 3

A. Synthesis of (3aS,4S,6aR)-1,3-dibenzyl-4-(ω,ω,ω-3-methoxycarbonyl butyl)-4H-1H-thiophene [3,4-d]iminazole-2,4(1H)-ketone (Formula A) (the intermediate 7)

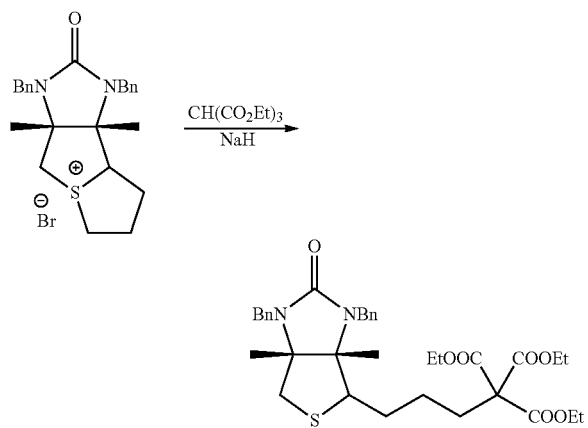

In a dry nitrogen-protection four-neck flask 500 ml with a reflux condenser, a dripping tube, a stirrer and a thermometer, the synthesis steps include adding 300 ml of methylbenzene and 60% of sodium hydride 3.3 g(0.0825 mol), dripping the catalyst 30 mL, controlling the inner temperature below 80 DEG C and dripping methane tricarboxylic acid trialkyl 19.3 g (0.083 mol), keeping heat preservation for 2 hours after dripping, cooling to the room temperature, adding bromine sulfonium onium salt 33.3 g (0.075 mol), heating and preserving and controlling the temperature at 80 DEG C to react for 15 hours, cooling to the room temperature, adjusting the pH to be around 3 by 5% of sulfuric acid, layering to obtain an organic layer, layering to obtain a water layer through reextraction by methylbenzene 100 mL, integrating the water layer into the organic layer, washing the organic layer twice by 5% of sodium bicarbonate water solution 40 mL, drying an oil layer by anhydrous sodium sulfate, filtering, depressurizing and recovering to obtain faint yellow liquid and getting a target product, tri-ester dibenzyl biotin 42.6 g(95.3% of the theoretical value) in the content 97.6% measured by HPLC and without the impurities 5.

B. Synthesis of the D-Biotin

In a three-neck flask 2000 mL, the synthesis steps of the D-biotin include injecting 42.5 g of the above-mentioned tri-ester dibenzyl biotin 7 and 48% of hydrobromic acid 800 g, stirring, refluxing and preserving the temperature at 125-126 DEG C for 8 hours, tracking the reaction until reaction (developer is methylbenzene—glacial acetic acid—methyl alcohol in the ratio 10:10:3(v/v/v)) is completed by the thin layer method, recovering the hydrobromic acid in vacuum, adjusting pH of residues to be 8 to 9 by 10% of sodium hydroxide, and cooling to be below 20 DEG C; weighing Bis(trichloromethyl) carbonate (BTC) 16 g to be dissolved by the methylbenzene 150 mL, slowly dripping the dissolved BTC into the above solution, keeping controlling the pH of the water layer to be 8 to 9 by the base during dripping, stirring for 1 hour after dripping, separating the organic layer, adjusting the pH of the water layer to be faintly acid by 10% of hydrochloric acid, precipitating to obtain crude biotin, filtering, recrystallizing the crude biotin by water and drying to obtain pure biotin 13.8 g in the content 98.7% measured by the HPLC and without the impurities 6 in the product.

Embodiment 4

A. Synthesis of (3aS,4S,6aR)-1,3-dibenzyl-4-(ω,ω,ω-3-methoxycarbonyl butyl)-4H-1H-thiophene [3,4-d]iminazole-2,4(1H)-ketone (Formula A) (the intermediate 7)

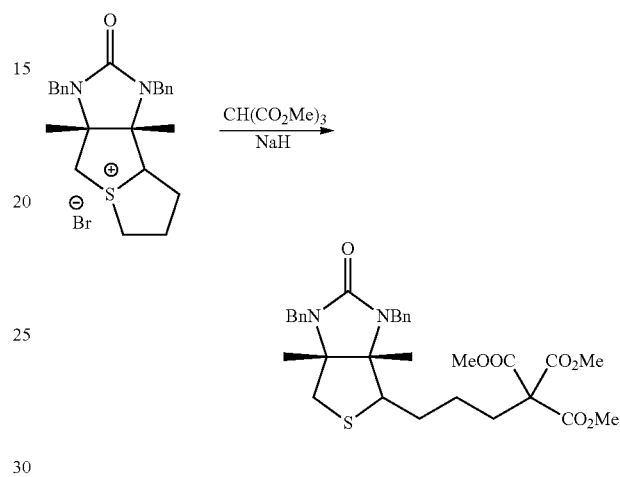

In a dry nitrogen-protection four-neck flask 500 ml with a reflux condenser, a dripping tube, a stirrer and a thermometer, the synthesis steps include adding 300 ml of methylbenzene and 60% of sodium hydride 3.3 g(0.0825 mol), dripping the catalyst 20 mL, controlling the inner temperature below 80 DEG C and dripping methane tricarboxylic acid trialkyl 15.8 g (0.083 mol), keeping heat preservation for 2 hours after dripping, cooling to the room temperature, adding bromine sulfonium onium salt 33.3 g (0.075 mol), heating and preserving and controlling the temperature at 80 DEG C to react for 15 hours, cooling to the room temperature, adjusting the pH to be around 3 by 5% of sulfuric acid, layering to obtain an organic layer, layering to obtain a water layer through reextraction by methylbenzene 100 mL, integrating the water layer into the organic layer, washing the organic layer twice by 5% of sodium bicarbonate water solution 40 mL, drying an oil layer by anhydrous sodium sulfate, filtering, depressurizing and recovering to obtain faint yellow liquid and getting a target product, tri-ester dibenzyl biotin 40.2 g(95.3% of the theoretical value) in the content 98.0% measured by HPLC and without the impurities 5.

B. Synthesis of the D-Biotin

In a three-neck flask 2000 mL, the synthesis steps of the D-biotin include injecting 40.2 g of the above-mentioned tri-ester dibenzyl biotin 7 and 48% of hydrobromic acid 800 g, stirring, refluxing and preserving the temperature at 125-126 DEG C for 8 hours, tracking the reaction until reaction (developer is methylbenzene—glacial acetic acid—methyl alcohol in the ratio 10:10:3(v/v/v)) is completed by the thin layer method, recovering the hydrobromic acid in vacuum, adjusting pH of residues to be 8 to 9 by 10% of sodium hydroxide, and cooling to be below 20 DEG C; weighing Bis(trichloromethyl) carbonate (BTC) 16 g to be dissolved by the methylbenzene 150 mL, slowly dripping the dissolved BTC into the above solution, keeping controlling the pH of the water layer to be 8 to 9 by the base during dripping, stirring for 1 hour after dripping, separating the organic layer, adjusting the pH of the water layer to be faintly acid by 10% of hydrochloric acid, precipitating to obtain crude biotin, filtering, recrystallizing the crude biotin by water and drying to obtain pure biotin 13.9 g in the content 98.6% measured by the HPLC and without the impurities 6 in the product.

Embodiment 5

A. Synthesis of (3aS,4S,6aR)-1,3-dibenzyl-4-(ω,ω,ω-3-methoxycarbonyl butyl)-4H-1H-thiophene [3,4-d]iminazole-2,4(1H)-ketone (Formula A) (the intermediate 7)

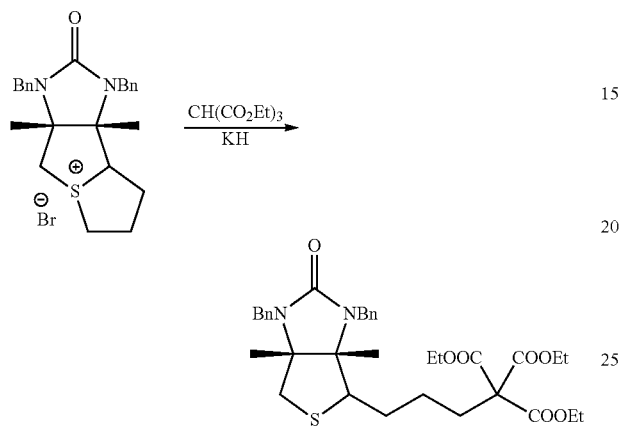

In a dry nitrogen-protection four-neck flask 500 ml with a reflux condenser, a dripping tube, a stirrer and a thermometer, the synthesis steps include adding 300 ml of methylbenzene and 40% of potassium hydride 8.3 g (0.0825 mol), dripping the catalyst 20 mL, controlling the inner temperature below 80 DEG C and dripping methane tricarboxylic acid trialkyl 19.3 g (0.083 mol), keeping heat preservation for 2 hours after dripping, cooling to the room temperature, adding bromine sulfonium onium salt 33.3 g (0.075 mol), heating and preserving and controlling the temperature at 80 DEG C to react for 15 hours, cooling to the room temperature, adjusting the pH to be around 3 by 5% of sulfuric acid, layering to obtain an organic layer, layering to obtain a water layer through reextraction by methylbenzene 100 mL, integrating the water layer into the organic layer, washing the organic layer twice by 5% of sodium bicarbonate water solution 40 mL, drying an oil layer by anhydrous sodium sulfate, filtering, depressurizing and recovering to obtain faint yellow liquid and getting a target product, tri-ester dibenzyl biotin 43.0 g (97.0% of the theoretical value) in the content 97.8% measured by HPLC and without the impurities 5.

B. Synthesis of the D-biotin

In a three-neck flask 2000 mL, the synthesis steps of the D-biotin include injecting 43.0 g of the above-mentioned tri-ester dibenzyl biotin 7 and 48% of hydrobromic acid 800 g, stirring, refluxing and preserving the temperature at 125-126 DEG C for 8 hours, tracking the reaction until reaction (developer is methylbenzene—glacial acetic acid—methyl alcohol in the ratio 10:10:3(v/v/v)) is completed by the thin layer method, recovering the hydrobromic acid in vacuum, adjusting pH of residues to be 8 to 9 by 10% of sodium hydroxide, and cooling to be below 20 DEG C; weighing Bis(trichloromethyl) carbonate (BTC) 16 g to be dissolved by the methylbenzene 150 mL, slowly dripping the dissolved BTC into the above solution, keeping controlling the pH of the water layer to be 8 to 9 by the base during dripping, stirring for 1 hour after dripping, separating the organic layer, adjusting the pH of the water layer to be faintly acid by 10% of hydrochloric acid, precipitating to obtain crude biotin, filtering, recrystallizing the crude biotin by water and drying to obtain pure biotin 14.0 g in the content 98.7% measured by the HPLC and without the impurities 6 in the product.

All the above-mentioned embodiments are only optimal ones of the D-biotin preparation method, which are not assumed as any forms of limitations for the D-biotin preparation method. Any simple modifications made according to the description and the content of the D-biotin preparation method are equivalently considered as transformations and embellishment and are included within the protection scope of the D-biotin preparation method without exception.

What is claimed is:

1. A method for preparing D-Biotin comprising following steps:
   (a) processing a condensation reaction for a compound of Formula B and a compound of methane tricarboxylic acid trialkyl ester in presence of dimethyl sulfoxide and an inorganic base of sodium hydride or potassium hydride in a toluene solvent, the usage of dimethyl sulfoxide is 5-10% in volume of the usage of toluene solvent, thereafter getting a compound of Formula A;

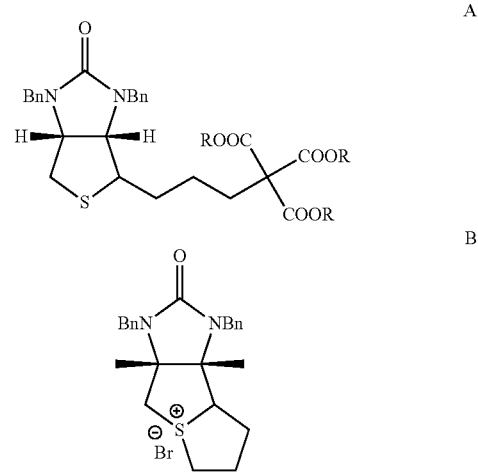

wherein the chemical formula of methane tricarboxylic acid trialkyl ester is $CH(COOR)_3$, wherein the R is an alkyl group comprising 1-5 carbon atoms, and the R on the three carboxylic acid groups are same or different alkyl groups;
   wherein the X is F or Cl or Br or I,
   (b) converting the compound of formula A to the D-Biotin by reaction processes of hydrolysis, decarboxylation and cyclization reaction for closing loop.

2. The D-biotin preparation method of claim 1, wherein the R in the chemical formula of the methane tricarboxylic acid trialkyl ester is methyl.

3. The D-biotin preparation method of claim 1, wherein the R in the chemical formula of the methane tricarboxylic acid trialkyl ester is ethyl.

4. The D-biotin preparation method of claim 1 comprises steps of:
   1) suspending the sodium hydride or potassium hydride in the toluene and dripping the dimethyl sulfoxide as the catalyst at the room temperature to obtain mixture;
   2) dripping the toluene solvent of the methane tricarboxylic acid trialkyl into the mixture to react and obtain methane tricarboxylic acid trialkyl sodium or methane tricarboxylic acid trialkyl potassium;
3) adding the solid compound of formula B into the product obtained in the step 2), heating to 80-110 DEG C. to react, sampling and detecting and stopping after complete reaction;
4) rinsing layer, recycling the toluene, adding hydrobromic acid to hydrolyze and obtain carboxylic acid, decarboxylating and debenzylating simultaneously, and finally cyclizing and purifying to obtain the D-biotin.

* * * * *